United States Patent

Young

(10) Patent No.: US 9,662,494 B2
(45) Date of Patent: May 30, 2017

(54) PROBE, ESPECIALLY A PROBE FOR NEURAL APPLICATIONS

(71) Applicant: MEDTRONIC BAKKEN RESEARCH CENTER B.V., Maastricht (NL)

(72) Inventor: Edward Willem Albert Young, Maastricht (NL)

(73) Assignee: Medtronic Bakken Research Center B.V., Maastricht (NL)

(*) Notice: Subject to any disclaimer, the term of this patent is extended or adjusted under 35 U.S.C. 154(b) by 0 days.

(21) Appl. No.: 14/436,397

(22) PCT Filed: Oct. 16, 2013

(86) PCT No.: PCT/EP2013/071632
§ 371 (c)(1),
(2) Date: Apr. 16, 2015

(87) PCT Pub. No.: WO2014/060478
PCT Pub. Date: Apr. 24, 2014

(65) Prior Publication Data
US 2015/0265835 A1     Sep. 24, 2015

Related U.S. Application Data

(60) Provisional application No. 61/714,386, filed on Oct. 16, 2012.

(30) Foreign Application Priority Data

Oct. 16, 2012   (EP) .................................. 12188693

(51) Int. Cl.
*A61N 1/36*     (2006.01)
*A61N 1/375*    (2006.01)
(Continued)

(52) U.S. Cl.
CPC ........ *A61N 1/3605* (2013.01); *A61B 5/04001* (2013.01); *A61B 5/0478* (2013.01); (Continued)

(58) Field of Classification Search
CPC ............ A61N 1/36125; A61N 1/36057; A61N 1/375; A61N 1/3606; A61N 1/3605; (Continued)

(56) References Cited

U.S. PATENT DOCUMENTS 5,324,322 A     6/1994   Grill, Jr. et al.
6,643,552 B2 *  11/2003  Edell ....................... A61N 1/05
                                                    600/373
(Continued)

FOREIGN PATENT DOCUMENTS

WO    2014060478 A1    4/2014

OTHER PUBLICATIONS

Hassler, et al., "Polymers for Neural Implants," Journal of Polymer Physics Science Part B: Polymer Physics, vol. 49, No. 1, Nov. 2010, pp. 18-33.

(Continued)

*Primary Examiner* — Deborah Malamud
(74) *Attorney, Agent, or Firm* — Shumaker & Sieffert, P.A.

(57) ABSTRACT

The present invention relates to a probe comprising at least one lead and an Advanced Lead Connector (ALC) element, the lead comprising at least one thin film, whereby the thin film comprises a proximal end and a distal end, the lead further comprising a plurality of electrodes on the distal end of the thin film, the ALC element comprising electronic means to address the plurality of electrodes and at least one ALC connecting means, whereby the proximal end of the thin film and the ALC connecting means are connected by an interposing means so as to form at least an electric and/or (Continued)

Figure 1:
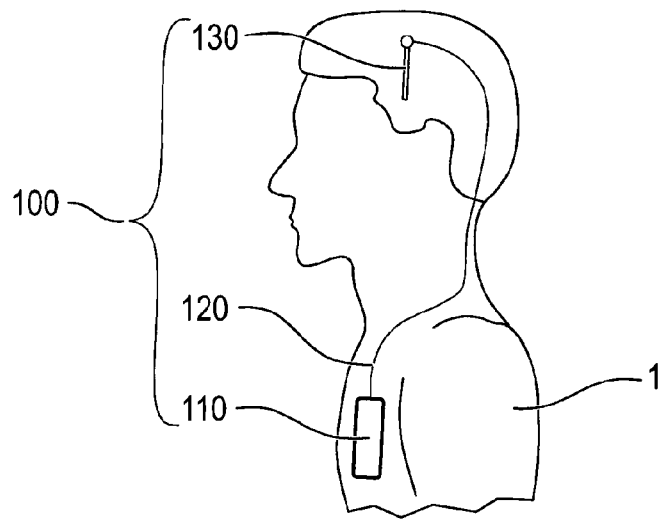

electronic connection between the electrodes and the ALC element. Furthermore, the present invention relates to a neurostimulation and/or neurorecording system, an interposing means, an assembly comprising at least one thin film for a lead of a probe and an ALC element and a method of manufacturing a probe.

21 Claims, 3 Drawing Sheets

(51) Int. Cl.
  *A61N 1/05*   (2006.01)
  *A61B 5/04*   (2006.01)
  *A61B 5/0478*   (2006.01)

(52) U.S. Cl.
  CPC ............ *A61N 1/05* (2013.01); *A61N 1/0534* (2013.01); *A61N 1/3754* (2013.01); *A61B 2562/0209* (2013.01); *A61B 2562/125* (2013.01); *A61B 2562/222* (2013.01); *A61B 2562/227* (2013.01); *A61N 1/0531* (2013.01); *Y10T 29/49169* (2015.01)

(58) Field of Classification Search
  CPC ...... A61N 1/3758; A61N 1/3754; A61N 1/08; A61N 1/3752; A61N 2005/0643; A61N 1/00; A61N 1/04; A61N 1/0488; A61B 5/04001; A61B 5/0478; A61B 2562/227; A61B 2562/0209; A61B 2562/125; A61B 2562/16; A61B 5/02427; A61B 2562/12; A61B 5/00; A61B 18/14; A61B 2018/00839; A61B 2562/02; A61B 2562/222; A61B 5/0082; A61B 5/02; A61B 5/02444; A61B 5/05; A61B 5/4047; H01L 23/055; Y10T 29/49018; Y10T 29/49002; Y10T 29/49169; B29L 2031/7542

See application file for complete search history.

(56) References Cited

U.S. PATENT DOCUMENTS

| | | |
|---|---|---|
| 2002/0198582 A1 | 12/2002 | Edell et al. |
| 2003/0100823 A1 | 5/2003 | Kipke et al. |
| 2007/0123765 A1 | 5/2007 | Hetke et al. |
| 2010/0274313 A1* | 10/2010 | Boling ................ A61N 1/0546 607/46 |
| 2011/0046470 A1 | 2/2011 | Kipke et al. |
| 2012/0185025 A1 | 7/2012 | Greenberg et al. |

OTHER PUBLICATIONS

Johnson, MD., et al., "Implantable microelectrode arrays for simultaneous electrophysiological and neurochemical recordings," Journal of Neuroscience Methods, vol. 174, No. 1, Sep. 2008, pp. 62-70 (19 pp. in provided document).
International Search Report and Written Opinion from International Application No. PCT/EP2013/071632, dated Jan. 7, 2014, 16 pp.

* cited by examiner

PROBE, ESPECIALLY A PROBE FOR NEURAL APPLICATIONS

The present invention relates to a probe, especially a probe for neural applications, preferably a probe for a neurostimulation and/or neurorecording system, further to a neurostimulation and/or neurorecording system, an interposing means, an assembly comprising at least one thin film for a lead of a probe and further comprising Advanced Lead Connector element and a method of manufacturing a probe.

Implantable neurostimulation devices have been used for the past ten years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In existing systems, the probes are connected to an implantable current pulse generator.

Currently, systems are under development with more, smaller electrodes in a technology based on thin film manufacturing. These novel systems consist of a lead made from a thin film based on thin film technology, as e.g. described in WO 2010/055453 A1. The thin film leads are fixed on a stylet material to form a probe. These probes will have multiple electrode areas and will enhance the precision to address the appropriate target in the brain and relax the specification of positioning. Meanwhile, undesired side effects due to undesired stimulation of neighbouring areas can be minimized.

Leads that are based on thin film manufacturing are e.g. described by U.S. Pat. No. 7,941,202 and have been used in research products in animal studies.

US 2002/0198582 A1 discloses an implantable medical device (IMD) that is formed on a substrate composed of liquid crystal polymer (LCP).

The use of thin films to create small electrodes for DBS has been described in literature (cf. Hassler, C. et al.; "Polymers for neural implants", JOURNAL OF POLYMER SCIENCE: PART B: POLYMER PHYSICS 2011, 49, 18-33). The thin film on the lead is connected to the electronics. For acute applications thin film can be connected to a flex foil to interface with the electronics or standard nylon housed pin connectors can be used for this purpose (cf. Hassler, C. et al.; "Polymers for neural implants", JOURNAL OF POLYMER SCIENCE: PART B: POLYMER PHYSICS 2011, 49, 18-33; and: Johnson, MD et al.; "Implantable microelectrode arrays for simultaneous electrophysiological and neurochemical recordings", Journal of Neuroscience Methods 174 (2008) 62-70).

However, in the case of an application for chronic use, a standard flex foil with electronic circuitry cannot be used because the electronics would be exposed to body fluids. Instead a connection to electronics in hermetic packaging that houses the electronics will have to be realized. The electrical interface on a hermetic package usually consists of ceramic feed-through with brazed though-hole pin connectors. State of the art feed-though ceramics have a rather limited pin density/unit area. As DBS systems with microelectrodes come with multiple micro electrodes, a lot of feed-though pins are needed and a large area is required to realize the interconnection.

Further, the thin film area is expensive. Moreover, a large area for connection to the feed-through is difficult to allocate on the mask when a wafer based manufacturing is applied.

Also, a thin film is rather fragile and the technology for interconnection does not marry well with the relatively large course pins on the ceramic feed-through of the Advanced Lead Connector.

It is therefore an object of the present invention, to improve a probe, further a neurostimulation and/or neurorecording system, an interposing means, an assembly comprising at least one thin film for a lead of a probe and further comprising Advanced Lead Connector element and a method of manufacturing a probe, particularly in that the connection between the thin film and the Advanced Lead Connector may be improved, that the overall reliability and safety of the whole system may be increased and that the production costs may be decreased.

The above object is solved according to the present invention by a thin film for a lead according to claim 1. Accordingly, a probe is provided comprising at least one lead and an Advanced Lead Connector (ALC) element, the lead comprising at least one thin film, whereby the thin film comprises a proximal end and a distal end, the lead further comprising a plurality of electrodes on the distal end of the thin film, the Advanced Lead Connector (ALC) element comprising electronic means to address the plurality of electrodes and at least one ALC connecting means, whereby the proximal end of the thin film and the ALC connecting means are connected by an interposing means so as to form at least an electric and/or electronic connection between the electrodes and the Advanced Lead Connector (ALC) element.

The probe, the lead and the thin film can be e.g. a probe, a lead and thin film for neural applications or, more specifically for brain applications, preferably for a a neurostimulation and/or neurorecording system. Such a neurostimulation and/or neurorecording system may be e.g. a DBS system. The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or merely the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which remote to the burr-hole of the skull, through which the lead is implanted.

The Advanced Lead Connector (ALC) element may be hermetically or merely hermetically sealed and may comprise electronic means to address the plurality of electrodes on the distal end of the thin film, which is arranged at the distal end and next to the distal tip of the lead. The plurality of electrodes may comprise more the 5-10 electrodes, e.g. 16 or 32 electrodes or in preferred embodiments e.g. 64 electrodes or more. The electrodes may be arranged such that the electrodes are merely evenly distributed arranged all over the distal end of the lead.

By this, the connection between the thin film and the Advanced Lead Connector may be improved, that the overall reliability and safety of the whole system may be increased and that the production costs may be decreased. In particular, on the one hand a plurality of electrodes may be realized in order to avoid side-effects and to provide a more accurate stimulation therapy when compared with prior art systems. On the other hand, the connection between the electrodes and the Advanced Lead Connector may be improved, since by means of the interposing means no large large area is required to realize the interconnection between the thin film and the interposing means and the connection between the interposing means and the ALC may be different and adapted to the needs to the relatively large course pins on the ceramic feed-through. Further, since no large connection area for the thin film connection is needed, also the production costs may be decreased. Material properties of the interposer can be selected to fit the needs of the preferred interconnection technology for interconnections at both ends, to the thin film and to the ceramic feed-through.

Furthermore, it is possible that the interposing means comprises a flexible foil with at least one metal track.

It is possible that the interposing means is a polyimide flexible printed circuit board (PCB). The use of non-medical grade materials e.g. metals such as Copper is best avoided. Also polyimide as a substrate material is less advisable for that reason.

Especially, the interposing means may comprise a parylene carrier and/or a polyimide carrier and/or a liquid crystal polymer carrier and/or one or more gold tracks. The parylene carrier may be e.g. a medical grade parylene carrier. Further, instead of gold tracks also suitable metal tracks may be used.

The interposer basically may consist of a standard flex foil (flexible printed circuit board, PCB). However, for medical device applications, it is advisable to use biocompatible materials such as gold metallization for the metal tracks and Parylene or liquid crystal polymer substrate as a carrier material.

Furthermore, it is possible that the connection between the proximal end of the thin film and the interposing means and/or the ALC connecting means and the interposing means is at least partially formed by wire bonding and/or rivet bonding. The rivet bonding may be e.g. rivet gold bonding. Also, stud bump bonding may be used or at least partially form the connection between the proximal end of the thin film and the interposing means and/or the ALC connecting means and the interposing means.

Moreover, it is possible that the connection between the proximal end of the thin film and the interposing means and/or the ALC connecting means and the interposing means is at least partially formed by soldering and/or laser welding.

Additionally, it is e.g. possible that the connection between the proximal end of the thin film and the interposing means and/or the ALC connecting means and the interposing means is at least partially formed by conductive glueing.

Further, it is possible that the ALC connecting means comprises a ceramic feed-through with one more course pins.

Especially, it is possible that the connection between the proximal end of the thin film and the interposing means has a smaller footprint than the connection between the ALC connecting means.

Moreover, it is possible that the interposing means has a greater thickness than the thin film. Thereby, the advantage may be achieved that the connection may be improved and the establishing process of the connection between the thin film and the interposing means may be facilitated.

Exemplarily, e.g. the flex foil of the interposing means may be thicker than the thin film and may have better mechanical properties and also the metallization of the interposing means may be thicker. Particularly, these features may facilitate the interconnection process when establishing the connection between the thin film and the interposing means.

Furthermore, the present invention relates to a neurostimulation and/or neurorecording system with the features of claim 11. Accordingly, a neurostimulation and/or neurorecording system is provided, especially a deep brain stimulation (DBS) system, comprising at least one a probe according to any of the preceding claims.

Additionally, the present invention relates to an interposing means with the features of claim 12. Accordingly, an interposing means is provided comprising the interposing means features according to any of the claims 1 to 10.

Further, the present invention relates to an assembly with the features of claim 13. Accordingly, an assembly is provided comprising at least one thin film for a lead of a probe and further comprising Advanced Lead Connector (ALC) element, the probe being the probe according to any of the claims 1 to 10, the thin film having the thin film features according to any of claims 1 to 10 and the Advanced Lead Connector (ALC) element having the Advanced Lead Connector (ALC) element features according to any of claims 1 to 10.

Moreover the present invention relates to a method of manufacturing a probe according to claim 14. Accordingly, the method of manufacturing a probe is conducted such that a probe is provided comprising at least one thin film and an Advanced Lead Connector element, the thin film comprises a proximal end and a distal end, the lead further comprising a plurality of electrodes on the distal end of the thin film, the Advanced Lead Connector (ALC) element comprising electronic means to address the plurality of electrodes and at least one ALC connecting means, and whereby the proximal end of the thin film and the ALC connecting means are connected by an interposing means so as to form at least an electric and/or electronic connection between the electrodes and the Advanced Lead Connector (ALC) element.

Exemplarily, the probe is a probe according to any of claims 1 to 10.

First, the film may be connected to the interposing means, i.e. a flex foil with metal tracks, using standard interconnect technology such as rivet bonding or using conductive glue for the electrical interconnect. As the pitch of the interconnect can be relatively fine, the area that is needed for this interconnect is small. Also, interconnection of two nice flat foils is a rather standard technology and does not pose new problems with e.g. topology. Next, the interconnect to the ceramic feed-through can be realized. The flex foil can be thicker than the thin film and has better mechanical properties and also the metallization can be thicker. These features will facilitate the interconnect process.

Figure 2:
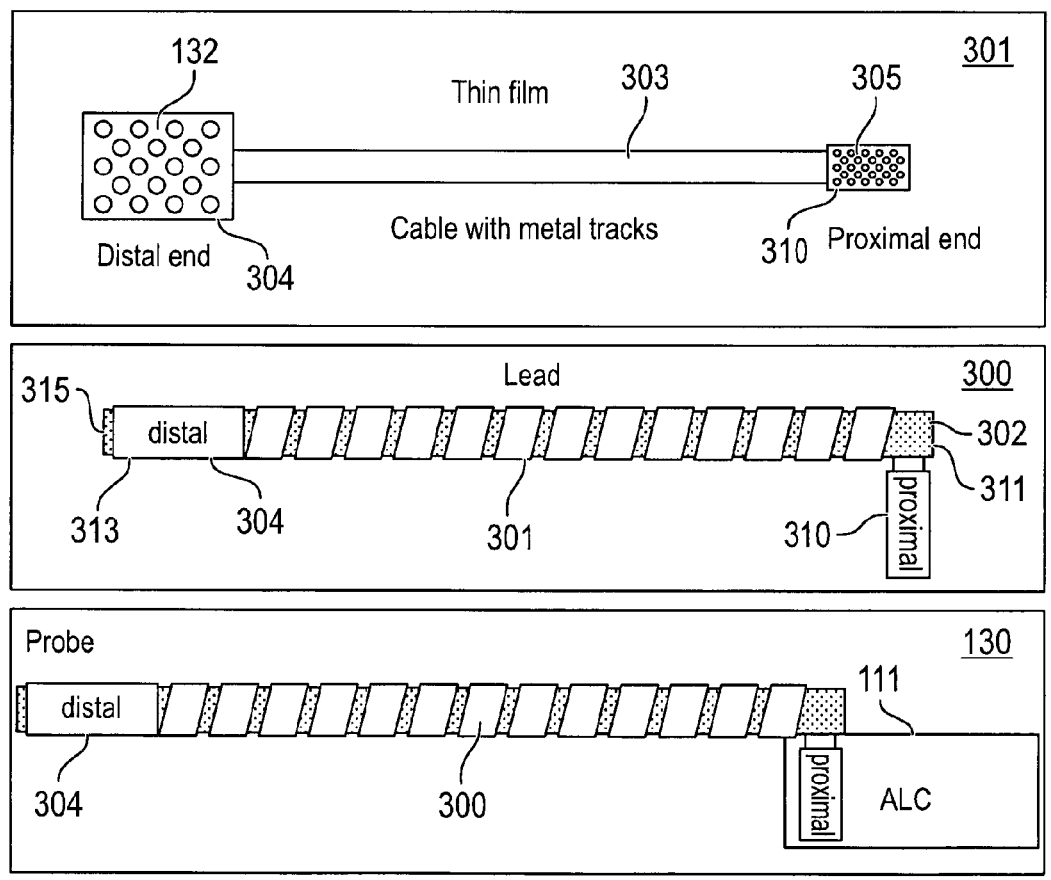
Figure 3:
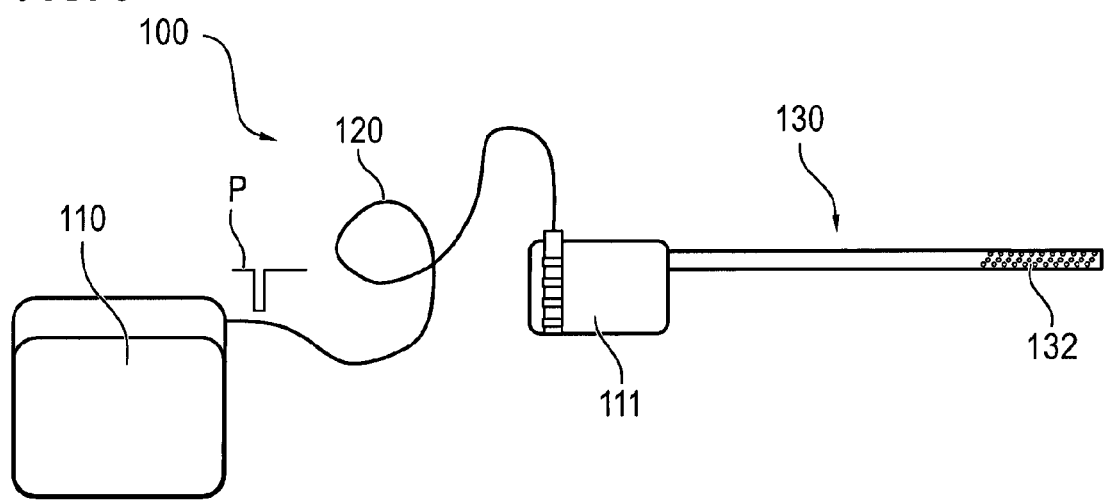
Figure 4:
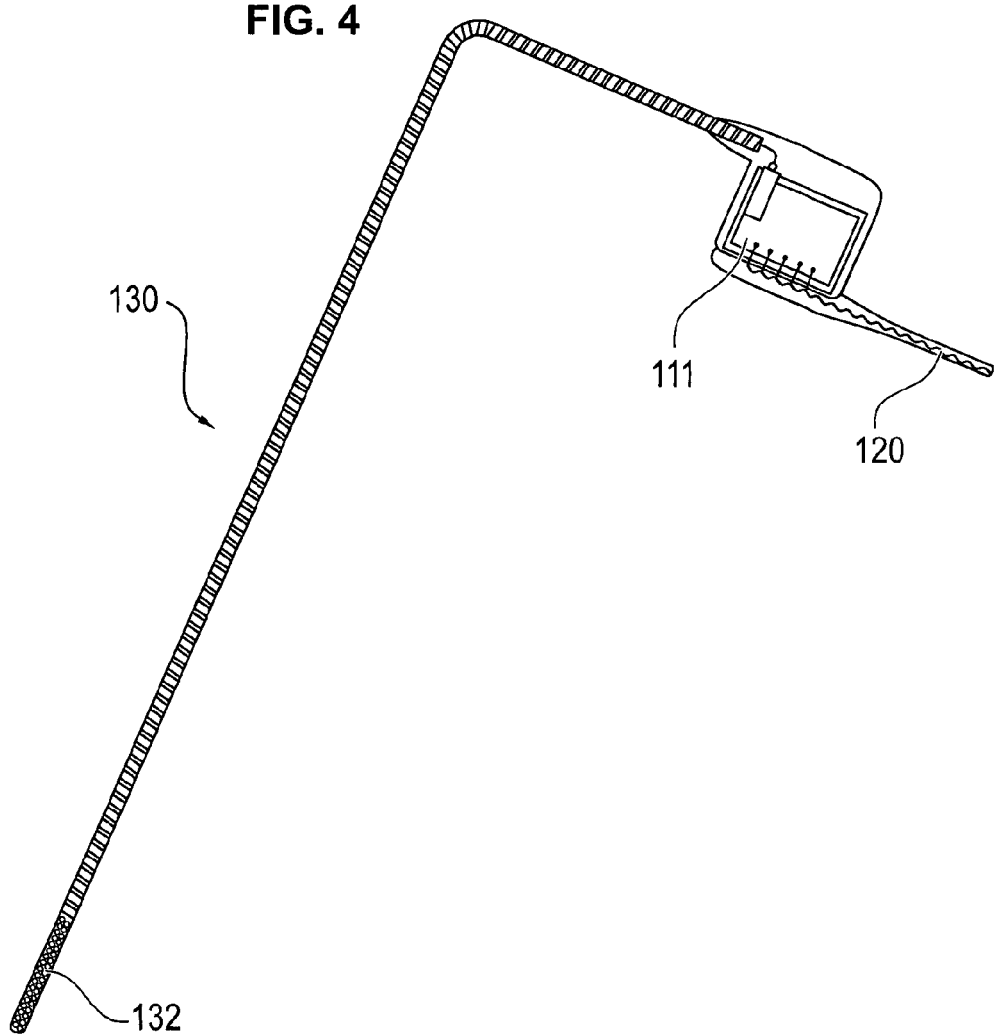
Figure 5:
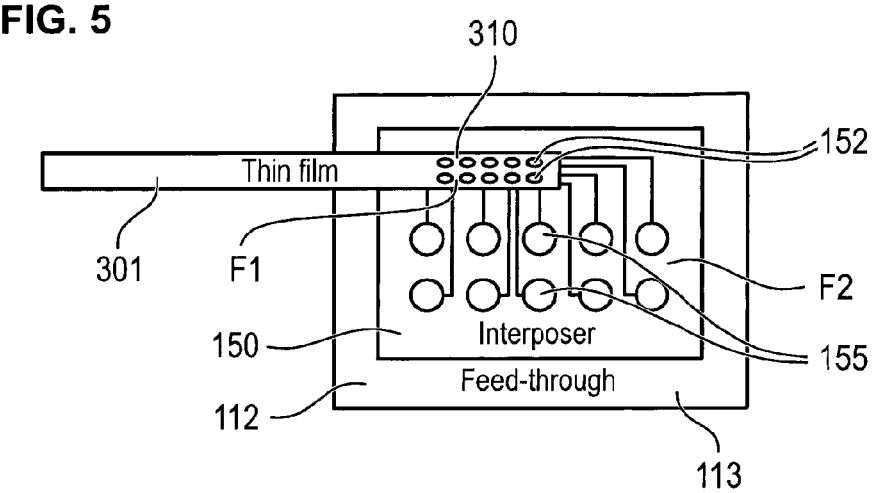
Figure 6:
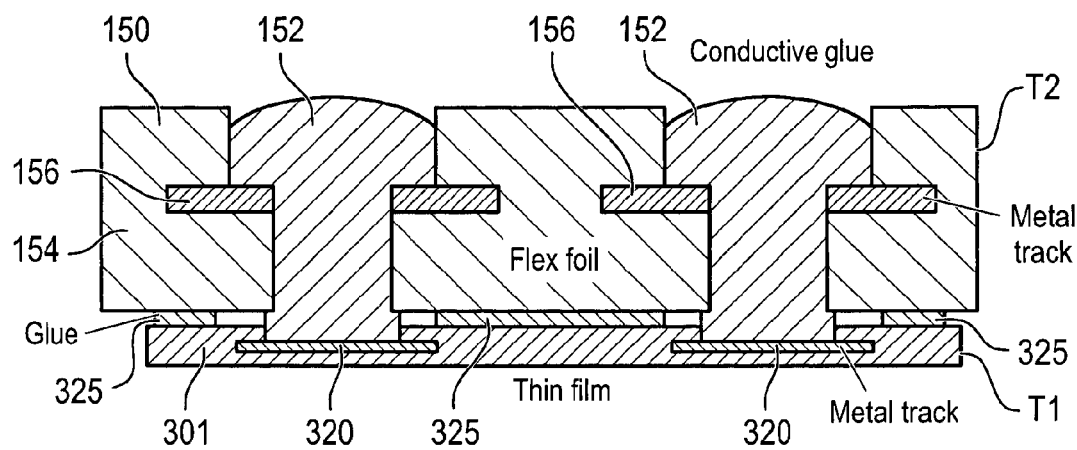
Figure 7:
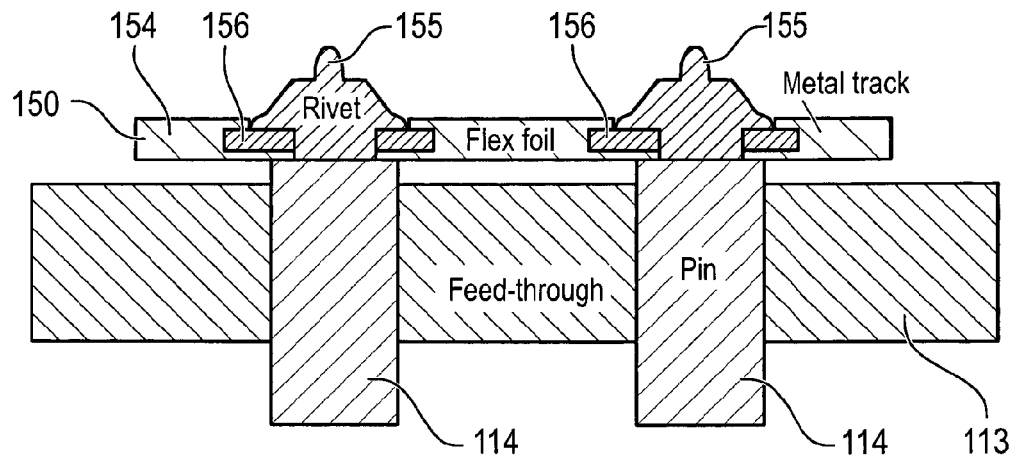

Further details and advantages of the present invention shall be described hereinafter with respect to the drawings:

FIG. 1: a schematical drawing of a neurostimulation system for deep brain stimulation (DBS);

FIG. 2: a further schematical drawing of a probe neurostimulation system for deep brain stimulation (DBS) and its components;

FIG. 3: a schematical drawing of a probe system according to the present invention;

FIG. 4: a further schematical drawing of probe system according to the present invention;

FIG. 5: a top-view of the connection of the thin film, the interposing means and the ALC connecting means;

FIG. 6: a schematical cross-sectional view of the connection between the thin film and the interposing means; and FIG. 7: a schematical cross-sectional view of the connection between the interposing means and the ALC connecting means.

A possible embodiment of a neurostimulation system 100 for deep brain stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

FIG. 2 further illustrates a typical architecture for a Deep Brain Stimulation probe 130 that comprises a DBS lead 300 and an Advanced Lead Connector (ALC) element 111 comprising electronic means to address electrodes 132 on the distal end 304 of the thin film 301, which is arranged at the distal end 313 and next to the distal tip 315 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the ALC element 111. The ALC element 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby e.g. 64 electrodes 132 can be provided on outer body surface at the distal end of the probe 130. By means of the extension wire 120 pulses P supplied by controller 110 can be transmitted to the ALC 111. The controller 110 can be an implantable pulse generator (IPG) 110.

FIG. 4 shows a schematical drawing of the probe 130 with the plurality of electrodes 132, the ALC element 111 and the extension wire 120 in a perspective view.

An example of the probe 130 according to the present invention is given in FIG. 5. This figure shows the interconnection of the thin film to the interposing means 150, here an interposer 150.

The proximal end 310 of the thin film 301 and the ALC connecting means 112 are connected by an interposing means 150 so as to form at least an electric and/or electronic connection between the electrodes 132 and the Advanced Lead Connector (ALC) element 111.

The connection between the proximal end 310 of the thin film 301 and the interposing means 150 has a smaller footprint F1 than the connection between the ALC connecting means 112. As shown in the example of FIG. 5, the footprint F1 is merely defined by the ten conductive glue connections 152. It is possible that each electrode 132 has its respective conductive glue connections 152. In other words, the number of electrodes 132 and the number of conductive glue connections 152 is preferably equal. However, dummy connection can be in place for mechanical anchoring. Alternatively, extra connections are reserved for connection to ground or high current feed-through ports are in parallel to reduce the current though each single one.

The ALC connecting means 112 comprises a ceramic feed-through 113 with one more course pins 114 (see also FIG. 7). The interconnect having a plurality of connections (here rivets 155, see also FIG. 7), here in the shown example ten connections, of the interposing means to the ALC ceramic feed-through 113 has a lager foot-print F2 as the pitch is much more wide. The number of the connections 155, the number of course pins 114 and the number of electrodes 132 and the number of conductive glue connections 152 is preferably equal. However, dummy connection can be in place for mechanical anchoring. Alternatively, extra connections are reserved for connection to ground or high current feed-through ports are in parallel to reduce the current though each single one.

An example to realize the interconnect between thin film 301 and the interposing means 150 is given in FIG. 6. FIG. 6 shows a conductive glue based interconnect according to the embodiment shown in FIG. 5. Alternatively, fine pitch interconnect technologies such as wire bonding and rivet bonding can be applied.

The interposing means 150 comprises a parylene carrier 154 or a liquid crystal substrate and several gold tracks 156. Preferably, the number of the gold tracks (respectively in other embodiments the number of all tracks) and the number of electrodes 132 may be equal. Thus, the number of the tracks, e.g. the number of the gold tracks 156, number of the connections 155, the number of course pins 114 and the number of electrodes 132 and the number of conductive glue connections 152 is preferably equal. The interposing means 150 of FIGS. 5 to 7 is a flexible printed circuit board (PCB).

The interposing means 150 has a greater thickness T2 than the thin film 301, which has a smaller thickness T1. Thereby, the advantage is achieved that the connection may be improved and the establishing process of the connection between the thin film 301 and the interposing means 150 may be facilitated.

Further, the interposing means 150 is partially arranged above the thin film 301, in other words, the interposing means 150 and the thin film 301 overlap partially.

The connection of the thin film 301 and the interposing means 150 is further stabilized by glue portions 325. The glue of the glue portions 325 is preferably a non-conductive glue.

The tracks 320, preferably gold tracks 320 of the thin film 301 are connected with the tracks 156 of the interposing means 150 by the conductive glue connections 152. The conductive glue connections 152 start from the upper side of the tracks 320 and extend through a hole in the metal track 156 of the interposing means. Further, the conductive glue connections 152 support the fixation of the track 156 by means of a mushroom-shaped head portion covering the hole in the upper side of the parylene carrier or liquid crystal polymer substrate 154, so that the metal tracks 156 of the interposing means are completely covered on the upper side of the interposing means 150.

Conductive glue is a preferred interconnect technology here because it does not require thick metal tracks in the thin film device An example to realize the interconnect between interposing means 150 and ALC element 111 is shown in FIG. 7 and according to the embodiment shown in FIG. 5. Alternatively, interconnect technologies such as wire bonding and conductive glue bonding or thermosonic ball-bonding may be applied. Also soldering technology and laser welding can be applied here FIG. 7 shows a rivet based interconnect between interposing means 150 and ALC element 111. Alternatively, interconnect technologies such as wire bonding and conductive glue bonding or thermosonic ball-bonding may be applied. Also soldering technology and laser welding can be applied here.

The interposing means 150 is partially arranged above the ceramic feed-through 113 and its course pins 114, in other words, the interposing means 150 and the ceramic feed-through 113 overlap partially.

The course pins 114 of the ceramic feed-through 113 of the ALC connecting means 112 are connected to the respective track 156 of the interposing means 150 by means of a rivet 155, which is bonded to at least the respective course pin 114 and also preferably and additionally to the respective metal track.

Above each interconnect position of a course pin 114, there a portions in the upper side of the parylene carrier or liquid crystal polymer substrate 154, into which the rivet 155 may be inserted. These portions are merely completely sealed by the inserted rivet 155 after the bonding process.

A possible application of the present invention is in the area of deep brain stimulation leads. DBS leads can be manufactured with thin films. The thin film is connected to the ALC. As stated above, the interconnect technology of a thin film to an ALC is difficult to realize. The use of an interposing means, e.g. an interposer spits the interconnect problem into two interconnects, the thin film to interposer interconnect and the interposer to ALC interconnect. As an optimal technology can be chosen now, both of them are relatively easy to realize. Consequently, the reliability and stability of the whole system and interconnect is improved and increased since, the interconnect may be realized in a relatively simple manner and the spit of one hardly matching interconnect into to well matching interconnects also helps to decrease the productions costs and facilitates the manufacturing process.

The invention claimed is:

1. A system for at least one of neurostimulation or neurorecording, the system comprising a probe comprising:
  at least one lead comprising at least one thin film, wherein the thin film comprises a proximal end and a distal end, the lead further comprising a plurality of electrodes on the distal end of the thin film; and
  an Advanced Lead Connector (ALC) element comprising means for electronically addressing the plurality of electrodes, a feed-through element, and a plurality of feed-through pins through the feed-through element for connecting the ALC element with the proximal end of the at least one thin film,
  wherein the proximal end of the thin film and the plurality of feed-through pins through the feed-through element are connected by an interposing element at least partially between the proximal end of the thin film and the plurality of feed-through pins so as to form at least one of an electric or electronic connection between the plurality of electrodes and the ALC element, a first plurality of connections between the proximal end of the thin film and the interposing element defining a first footprint smaller than a second footprint defined by a second plurality of connections between the interposing element and the plurality of feed-through pins through the feed-through element, and wherein the first plurality of connections and the second plurality of connections are disposed at least partially through the interposing element.

2. The system according to claim 1, wherein the interposing element comprises a flexible foil with at least one metal track.

3. The system according to claim 2, wherein the interposing element comprises a flexible printed circuit board (PCB).

4. The system according to claim 1, wherein the interposing element comprises one or more of a parylene carrier, a polyimide carrier, a liquid crystal polymer carrier, or one or more gold tracks.

5. The system according to claim 1, wherein one or more of the first plurality of connections between the proximal end of the thin film and the interposing element or the second plurality of connections between the interposing element and the plurality of feed-through pins is at least partially formed by one or more of wire bonding, rivet gold bonding, or stud bump bonding.

6. The system according to claim 1, wherein one or more of the first plurality of connections between the proximal end of the thin film and the interposing element or the second plurality of connections between the interposing element and the plurality of feed-through pins is at least partially formed by one or more of soldering or laser welding.

7. The system according to claim 1, wherein one or more of the first plurality of connections between the proximal end of the thin film and the interposing element or the second plurality of connections between the interposing element and the plurality of feed-through pins is at least partially formed by a conductive glue.

8. The system according to claim 1, wherein the feed-through element comprises a ceramic feed-through element with the plurality of feed-through pins, the plurality of feed-through pins electrically coupled to a respective connection of the second plurality of connections.

9. The system according to claim 1, wherein the interposing element has a thickness greater than the thin film.

10. The system of claim 1, wherein the system is configured to deliver deep brain stimulation (DBS) via the probe.

11. The system of claim 1, further comprising a controller configured to supply electrical stimulation pulses to the ALC element.

12. The system of claim 11, wherein the ALC element comprises a switch matrix that distributes the electrical stimulation pulses to selected electrodes of the plurality of electrodes.

13. The system of claim 11, further comprising a wire connected to the controller and the ALC element.

14. The system of claim 11, wherein the controller comprises an implantable pulse generator.

15. The system of claim 1, wherein the means for electronically addressing the plurality of electrodes comprises means for switching outputs from a pulse generator across one or more electrodes of the plurality of electrodes to deliver stimulation pulses.

16. The system of claim 1, wherein the at least one thin film at least partially overlaps the interposing element, and wherein the interposing element overlaps a portion of the feed-through element comprising the plurality of feed-through pins.

17. An assembly comprising:
- at least one thin film for a lead of a probe, the thin film comprising a proximal end and a distal end, and wherein a plurality of electrodes are disposed on the distal end of the thin film; and
- an Advanced Lead Connector (ALC) element configured to electronically address the plurality of electrodes, the ALC element comprising a feed-through element and a plurality of feed-through pins through the feed-through element configured to connect the ALC element with an interposing element; and
- the interposing element configured to form an electrical connection between the plurality of electrodes and the ALC element via the plurality of feed-through pins through the feed-through element, at least a portion of the interposing element disposed between the proximal end of the thin film and the plurality of feed-through pins, wherein a first plurality of connections between the proximal end of the thin film and the interposing element defines a first footprint smaller than a second footprint defined by a second plurality of connections between the interposing element and the plurality of feed-through pins through the feed-through element of the ALC element, and wherein the first plurality of connections and the second plurality of connections are disposed at least partially through the interposing element.

18. The assembly of claim 17, wherein the ALC element comprises a switch matrix configured to switch outputs from a pulse generator across one or more electrodes of the plurality of electrodes.

19. The assembly of claim 17, wherein the first plurality of connections comprises, for each of the plurality of electrodes, a conductive glue configured to electrically connect the distal end of the thin film and the interposing element.

20. The assembly of claim 17, wherein the second plurality of connections comprises, for each of the plurality of electrodes, a respective feed-through pin of the plurality of feed-through pins configured to electrically connect the ALC element to the interposing element.

21. A method of manufacturing a probe, the probe comprising at least one thin film and an Advanced Lead Connector (ALC) element, the thin film comprising a proximal end and a distal end, the probe further comprising a plurality of electrodes on the distal end of the thin film, and the ALC element comprising electronic means for addressing the plurality of electrodes, a feed-through element, and a plurality of feed-through pins through the feed-through element configured to connect the ALC element with an interposing element, wherein the method comprises:
- electrically coupling the plurality of feed-through pins through the feed-through element to an interposing element to form one or more first connections, the one or more first connections disposed at least partially through the interposing element; and
- electrically coupling the proximal end of the thin film to the interposing element to form one or more second connections, the one or more second connections disposed at least partially through the interposing element, and the one or more first connections and the one or more second connections forming at least electric and/or electronic connections between the plurality of electrodes and the ALC element, wherein the one or more second connections define a first footprint smaller than a second footprint defined by the one or more first connections, and wherein the interposing element is at least partially between the proximal end of the thin film and the plurality of feed-through pins.

* * * * *